(12) United States Patent
Malzkorn et al.

(10) Patent No.: US 7,439,413 B2
(45) Date of Patent: Oct. 21, 2008

(54) METHOD FOR THE PRODUCTION OF ISOBUTENE FROM COMMERICIAL METHYL TERT-BUTLY ETHER

(75) Inventors: Rainer Malzkorn, Dorsten (DE); Franz Nierlich, Marl (DE); Udo Peters, Marl (DE); Axel Tuchlenski, Weinheim (DE)

(73) Assignee: OXENO Olefinchemie GmbH, Marl (DE)

( * ) Notice: Subject to any disclaimer, the term of this patent is extended or adjusted under 35 U.S.C. 154(b) by 611 days.

(21) Appl. No.: 10/524,790

(22) PCT Filed: Jul. 11, 2003

(86) PCT No.: PCT/EP03/07543

§ 371 (c)(1),
(2), (4) Date: Feb. 16, 2005

(87) PCT Pub. No.: WO2004/018393

PCT Pub. Date: Mar. 4, 2004

(65) Prior Publication Data

US 2006/0135833 A1 Jun. 22, 2006

(30) Foreign Application Priority Data

Aug. 22, 2002 (DE) .................. 102 38 370

(51) Int. Cl.
*C07C 1/00* (2006.01)
*C07C 7/00* (2006.01)
(52) U.S. Cl. .................. 585/639; 585/640; 585/809

(58) Field of Classification Search ................. 585/639, 585/640, 809
See application file for complete search history.

(56) References Cited

U.S. PATENT DOCUMENTS

| 4,570,026 | A | * | 2/1986 | Keyworth et al. ........... 585/312 |
| 5,095,164 | A | * | 3/1992 | Gabel et al. ................. 585/640 |
| 5,348,710 | A | | 9/1994 | Johnson et al. |
| 5,518,699 | A | * | 5/1996 | Kashnitz et al. ............. 422/211 |
| 5,567,860 | A | | 10/1996 | Mowry et al. |
| 6,552,236 | B2 | | 4/2003 | Sakuth et al. |

FOREIGN PATENT DOCUMENTS

| DE | 35 09 292 | 12/1985 |
| DE | 240 739 | 11/1986 |
| DE | 36 10 704 | 10/1987 |
| DE | 43 22 712 | 1/1995 |

(Continued)

OTHER PUBLICATIONS

U.S. Appl. No. 11/614,275, filed Dec. 21, 2006, Praefke, et al.

(Continued)

*Primary Examiner*—Glenn Caldarola
*Assistant Examiner*—In Suk Bullock
(74) *Attorney, Agent, or Firm*—Oblon, Spivak, McClelland, Maier & Neustadt, P.C.

(57) ABSTRACT

The invention relates to a process for preparing high-purity isobutene from industrial methyl tert-butyl ether (MTBE) and the economical utilization of the secondary streams.

20 Claims, 3 Drawing Sheets

FOREIGN PATENT DOCUMENTS

| | | |
|---|---|---|
| DE | 100 20 943 | 10/2001 |
| DE | 101 02 082 | 5/2002 |
| EP | 0 302 336 | 2/1989 |
| EP | 0 428 265 | 5/1991 |
| EP | 0 433 222 | 6/1991 |
| EP | 0 950 433 | 10/1999 |
| WO | 98/06684 | 2/1998 |

OTHER PUBLICATIONS

U.S. Appl. No. 11/838,340, filed Aug. 14, 2007, Winterberg, et al.
U.S. Appl. No. 11/839,604, filed Aug. 16, 2007, Winterberg, et al.
U.S. Appl. No. 11/758,285, filed Jun. 5, 2007, Winterberg, et al.
U.S. Appl. No. 11/836,905, filed Aug. 10, 2007, Zanthoff, et al.
U.S. Appl. No. 11/839,597, filed Aug. 16, 2007, Fernandez, et al.

* cited by examiner

METHOD FOR THE PRODUCTION OF ISOBUTENE FROM COMMERICIAL METHYL TERT-BUTLY ETHER

The invention relates to a process for preparing high-purity isobutene from industrial methyl tert-butyl ether (MTBE) and the economical utilization of the secondary streams.

Isobutene is a starting material for the production of butyl rubber, polyisobutylene, isobutene oligomers, branched $C_5$-aldehydes and $C_5$-carboxylic acids. Furthermore, it is used as alkylating agent and intermediate for the production of peroxides.

Isobutene can be obtained by dehydrogenation of isobutane. However, sufficiently large amounts of pure isobutane are not available.

In industrial streams, for example, in the $C_4$ fraction from a steam cracker or an FCC unit, isobutene is present together with saturated and unsaturated hydrocarbons. Owing to the small boiling point difference or the very low separation factor between isobutene and 1-butene, isobutene cannot be separated economically from these mixtures by distillation.

The isobutene can be separated off from these $C_4$ fractions in various ways, depending on which further olefins are to be obtained. The first step which is common to all work-up methods is removal of the major part of the butadiene and other multiply unsaturated hydrocarbons. If butadiene can readily be marketed or there is an in-house demand, it is separated off by extraction or extractive distillation. Otherwise, it is selectively hydrogenated to linear butenes down to a residual concentration of about 2000 ppm by mass. In both cases, the stream which remains is a hydrocarbon mixture (known as raffinate I or hydrogenated cracking $C_4$) which comprises the saturated hydrocarbons n-butane and isobutane together with the olefins isobutene, 1-butene and 2-butenes (cis and trans).

If 2-butene or a mixture of linear butenes having a high 2-butene content is to be obtained in addition to isobutene, the abovementioned mixture, which typically contains not more than 1% of butadiene ($C_4$ stream from FCC, raffinate I or hydrogenated cracking $C_4$), is hydrogenated and hydroisomerized, i.e. residual butadiene still present is selectively hydrogenated down to a residual content of below 5 ppm and 1-butene is isomerized to the 2-butenes. The equilibrium ratio of 1-butene to the two 2-butenes is, for example, about 1/17, i.e. far on the side of the 2-butenes, at 80° C. Owing to the small boiling point differences, distillation of the hydroisomerization mixture gives only a mixture of isobutene, 1-butene and isobutane as top product, from which the isobutane can be separated off by distillation. The bottom product obtained is an isobutene-free mixture comprising 2-butenes. Even if the hydroisomerization is carried out in a reactive distillation column, no completely 1-butene-free isobutene is obtained, as described, for example, in EP 0 922 018. This isobutene is therefore not suitable for some applications.

Isobutene can be separated off from a $C_4$-olefin mixture via the steps selective conversion into a derivative, separation of the derivative from the remaining hydrocarbon mixture and dissociation of the derivative.

Isobutene can easily be converted into derivatives by means of water or alcohols. The reaction of isobutene-containing streams with water gives tert-butanol (TBA) which can easily be redissociated into isobutene and water. The main disadvantage of this separation process is the TBA synthesis, which, owing to the low solubility of water in $C_4$-hydrocarbons, gives only low space-time yields.

The addition of methanol onto isobutene in $C_4$-hydrocarbon streams to form MTBE proceeds substantially more quickly than the addition of water. Industrial MTBE is a valued fuel component for four-stroke engines for the purpose of increasing the octane number. Owing to the ease with which it can be prepared and its large market volume, it is an inexpensive precursor for pure isobutene.

For this reason, the industrial procedure is usually to react an isobutene-containing $C_4$ fraction with methanol to form MTBE, purify the latter and redissociate it into isobutene and methanol.

This process has the disadvantage that it is difficult to prepare isobutene having a purity of greater than 99.9%. Industrial MTBE (fuel grade) further comprises $C_4$- and $C_5$-hydrocarbons, $C_4$-oligomers ($C_8$-, $C_{12}$-hydrocarbons), 2-methoxybutane (MSBE), methanol and TBA. These materials and their downstream products and also other by-products formed from MTBE during the dissociation can contaminate the target product isobutene.

Integrated processes for preparing high-purity isobutene from $C_4$-streams via the preparation of MTBE and its dissociation are known and described, for example, in U.S. Pat. No. 5,567,860. Here, isobutene-containing $C_4$ streams are firstly etherified with methanol to give, depending on the conversion, a mixture of MTBE, MSBE, unreacted $C_4$-hydrocarbons, methanol, water, DME, $C_4$ oligomers and also $C_3$- and $C_5$-hydrocarbons as contaminants in the $C_4$ stream. This product mixture is fractionally distilled to give a low-boiling fraction comprising the $C_3$-, $C_4$- and $C_5$-hydrocarbons, methanol and DME and a high-boiling fraction comprising $C_4$ oligomers. MTBE and MSBE are obtained in a side stream taken from the column and are then passed to the acid-catalyzed dissociation. The dissociation reaction accordingly gives isobutene, n-butene and methanol as main constituents together with unreacted MTBE and MSBE. This product mixture is in turn purified by distillation, with the $C_4$/methanol azeotrope comprising isobutene and n-butene and DME being taken off as low-boiling fraction. To obtain the target product, viz. high-purity isobutene, this fraction has to be purified by means of at least one water scrub and a distillation. The high-boiling fraction obtained from the dissociation reaction (MTBE, methanol, MSBE) is fractionated to give methanol as high boiler and an azeotrope of methanol, MTBE and MSBE as low boiler. These fractions are each recirculated to a point upstream of the etherification stage or the dissociation stage.

This process is complicated in that the target product isobutene has to be freed of the accompanying substances in the $C_4$ feed stream and unreacted reaction products or by-products from the etherification and dissociation reactions in a plurality of columns and scrubbing stages. Furthermore, an integrated process should make it possible for unreacted materials such as MTBE or isobutene-containing $C_4$ streams to be separated off in a simple fashion and be recirculated to the appropriate reaction stages. In the ideal case, isobutene-containing $C_4$ hydrocarbons and recovered methanol would be separated off at a point in the process and reused for the preparation of MTBE. On the other hand, unreacted MTBE should be obtained as a separate stream and be recirculated to the ether dissociation reaction.

It is therefore an object of the present invention to provide a process for preparing isobutene from MTBE which can be operated using very few separation stages and with few recycle streams.

The present invention accordingly provides a process for preparing isobutene by acid-catalyzed dissociation of methyl tert-butyl ether (MTBE), which comprises
fractionating a feed mixture comprising MTBE, $C_4$- and $C_5$-hydrocarbons, methanol, methyl sec-butyl ether, TBA and $C_4$ oligomers to give
a) a fraction a) comprising MTBE, MSBE, TBA and $C_4$ oligomers and
b) a fraction b) comprising $C_4$- and $C_5$-hydrocarbons, MTBE and methanol,
c) dissociating the MTBE present in the fraction a) into methanol and isobutene and
d) separating off an isobutene-containing stream from the dissociation product from c) and recirculating the remainder to the feed mixture.

The MSBE present in the feed mixture passes unspecifically into the two fractions a) and b), but is removed in an advantageous fashion by means of a bleed stream from the fraction a).

The process of the invention can easily be linked to an existing MTBE plant, so that the recycle streams of methanol and $C_4$-hydrocarbons can be reused for the preparation of MTBE. It is also possible to use industrial MTBE of fuel quality or with even lower specifications.

Compared to the prior art, the process of the invention achieves a particularly elegant removal of impurities present in the feed mixture and streams to be recirculated to other process stages. Thus, methanol and low-boiling impurities in the feed mixture are separated off in the first distillation stage prior to the dissociation reaction. This makes it possible for the isobutene obtained in the dissociation reaction to be separated off efficiently, since interfering accompanying materials have already been separated off. The recirculation of the methanol obtained in the reaction to upstream of the dissociation reaction, or more precisely upstream of the first distillation stage, results in efficient circulation of the methanol with simultaneous removal of by-products such as DME, $C_4$ oligomers, TBA or MSBE in an MTBE synthesis preceding the process of the invention.

Figure 1:
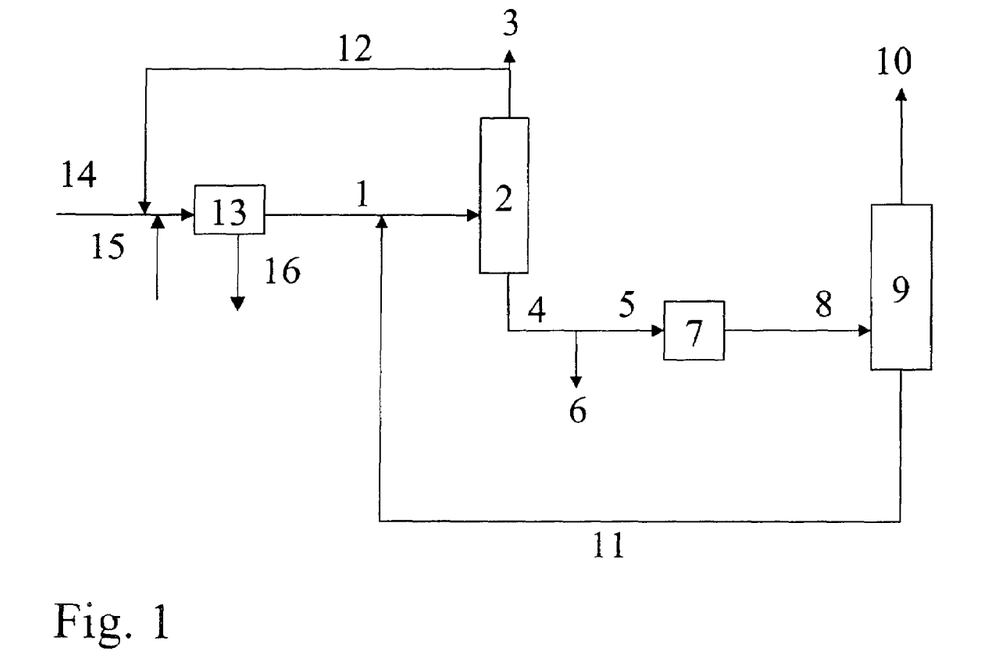
FIG. 1 shows a block diagram according to the invention.

A block diagram of a plant in which the process of the invention can be carried out is shown in FIG. 1. MTBE (fuel grade) (1) together with the bottom product (11) from column (9) is fed into the column (2). A mixture of MTBE, methanol and $C_4$- and $C_5$-hydrocarbons is taken off as top product (3). A part (6) of the bottom product (4) from the column (2), which comprises predominantly MTBE, is separated off to discharge high boilers (TBA, diisobutene, MSBE). The other part (5) is fed to the dissociation reactor (7). The reaction mixture (8) is fractionated in the distillation column (9). The top product (10) obtained is an isobutene which may further comprise methanol, dimethyl ether and water. The optional work-up of this crude isobutene to give high-purity isobutene is not shown in FIG. 1. The bottom product (11) from the column (9), which comprises undissociated MTBE, part of the methanol formed in the dissociation and high boilers, is recirculated to the column (2). In place of the reactor (7) and the column (9), it is also possible to use one or more reactive distillation columns. All or part of the stream (3) can be conveyed via line (12) to an optional etherification stage (13). Here, MTBE is prepared from an isobutene-containing $C_4$-hydrocarbon stream (14), fresh methanol (15) and the recirculated methanol (12). Stream (16) serves to bleed off unreacted components from the isobutene-containing $C_4$-hydrocarbon stream (e.g. n-butene and aliphatic constituents).

The feed to the process of the invention can be industrial MTBE of fuel grade. This typically comprises 98% by mass of MTBE together with about 0.5% by mass of $C_4$- to $C_8$-hydrocarbons, about 1% by mass of methanol, about 500 ppm by mass of water and 2-methoxybutane. Preference is given to using an industrial MTBE having a 2-methoxybutane content of less than 2500 ppm by mass, whose preparation is described, for example, in DE 101 02 082.

It is also possible to use MTBE grades having a methanol content significantly higher than 1% by mass, e.g. MTBE/methanol mixtures having a ratio of 80:20, 90:10 or 95:5 can be processed without problems. These mixtures can naturally further comprise the accompanying materials mentioned above in an amount of ≦3% by weight.

In the process of the invention, the $C_4$- and $C_5$-hydrocarbons in the MTBE are removed by distillation together with the MTBE-methanol minimum azeotrope. This gives a distillate comprising MTBE, methanol and $C_4$- and $C_5$-hydrocarbons. This mixture is advantageously fed to the synthesis stage of an MTBE plant.

As a result of the recirculation of the bottom product (11) from the distillation column (9), the $C_4$- and $C_5$-hydrocarbons are removed from the MTBE feed in the column (2) and the major part of the methanol formed in the MTBE dissociation is also separated off in this column.

It has in practice been found to be useful for the distillation column upstream of the dissocation reactor ((2) in FIG. 1) to have from 10 to 60 theoretical plates, in particular from 20 to 40 theoretical plates, of which from 10 to 30 are in the enrichment section and from 10 to 30 are in the stripping section.

The column is advantageously provided with internals such as trays, random packing or ordered packing. The fractionation in this column can be carried out at atmospheric pressure or under superatmospheric pressure. Since the proportion of MTBE in the MTBE/methanol azeotrope decreases with increasing pressure in the pressure range from 1 to 25 bar and as little MTBE as possible should be separated off together with the methanol, the distillation is preferably carried out under superatmospheric pressure, in particular in the pressure range from 5 to 25 bar, very particularly preferably in the pressure range from 8 to 20 bar.

The reflux ratio in the column is from 1 to 10, in particular from 2 to 7.

The bottom product from the column (2) upstream of the dissociation reactor (step a) (FIG. 1) preferably has a content of $C_4$- and $C_5$-hydrocarbons of less than 250 ppm by mass. It contains a small amount of methanol and also TBA, 2-methoxybutane and diisobutene as high boilers.

To separate off $C_4$- and $C_5$-hydrocarbons, their oligomers and methanol from the dissociation together and at the same time prevent accumulation of high boilers in the process, a part (6) of the bottom product (4) from the column (2) can be bled off continuously. The discharge of the $C_4$ oligomers from the fraction a) of the process of the invention can be carried out either by means of a bleed stream or by means of a further distillation stage, e.g. as bottom product. One possible use for the bleed stream is work-up by distillation to produce high-purity MTBE. For this it is necessary to reduce the methanol content of the bottoms (4) from the column (2) to 50 ppm by mass, which can be achieved by taking off an increased amount of distillate from the column (2).

The dissociation of the bottom product, which comprises predominantly MTBE, into isobutene and methanol can be carried out over an acid catalyst located in a fixed bed.

One group of acid catalysts which can be used in the process of the invention are solid ion exchange resins bearing sulfonic acid groups.

Suitable ion exchange resins are, for example, those which are prepared by sulfonation of phenol/aldehyde condensates or of cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. In particular, the cooligomers formed by reaction of styrene with divinylbenzene are used as intermediate for the preparation of ion exchange resins bearing sulfonic acid groups. The resins can be prepared in gel form, macroporous form or sponge form. Strong acid resins of the styrene-divinylbenzene type are sold, inter alia, under the following trade names: Duolite C20, Duolite C26, Amberlyst A15, Amberlyst A35, Amberlyst 36, Amberlite IR-120, Amberlite 200, Dowex 50, Lewatit K2431, Lewatit K2441, Lewatit K2621, Lewatit K2629, Lewatit K2641.

The properties of these resins, in particular the specific surface area, porosity, stability, swelling or shrinkage and exchange capacity, can be varied by means of the production process.

If desired, it is also possible to use commercial, macroporous cation exchangers which have been modified by partial ion exchange or by thermal desulfonation.

The dissociation of MTBE is carried out in one or more reactors. When a plurality of reactors are used, these can be connected in series or in parallel or both in series and in parallel. it is possible to use various types of reactor, for example fixed-bed reactors or shell-and-tube reactors or kettle reactors.

The reactor(s) is/are operated isothermally, polytropically or adiabatically, in a single pass or with an external recycle loop.

The reaction temperature in the dissociation reactor in the process of the invention is in the range from 60° C. to 200° C., preferably from 80° C. to 120° C. When a plurality of reactors are used, the temperatures can be identical or different.

The dissociation of MTBE can be carried out in the liquid phase over acid ion exchange resins as described, for example, in DE 3 509 292 or DE 3 610 704 or over acidic aluminum oxides as disclosed, for example, in DD 240 739. In the latter case, the reaction conditions (167° C. and 1 bar or 297° C. and 10 bar) are selected so that the dissociation of MTBE can also proceed in the gas/liquid region. However, in the case of dissociation processes carried out in the pure liquid phase, it has to be noted that high MTBE conversions cannot be achieved in a single pass because of the position of the thermodynamic equilibrium. If pure MTBE is used in a dissociation reaction which is preferably to proceed at 100° C., an equilibrium conversion of about 15 mol % is obtained on the basis of the thermodynamics. A problem in the dissociation in the liquid phase is the isobutene which is dissolved in the homogeneous liquid phase and can undergo further reactions. The most important further reactions of this type are acid-catalyzed dimerization and oligomerization. For this reason, undesirable $C_8$ and $C_{12}$ components are found together with the desired target product isobutene. The undesirable $C_8$ molecules are 2,4,4-trimethyl-1-pentene and 2,4,4-trimethyl-2-pentene. High reaction temperatures also favor the undesirable secondary reaction of methanol to form dimethyl ether (DME). The formation of dimethyl ether not only leads to a loss of methanol but also increases the difficulty of purifying the isobutene.

The MTBE dissociation reaction can also be carried out in a reaction distillation column, as disclosed in EP 0 302 336 or DE 4 322 712. EP 0 302 336 describes the elimination of methanol from MTBE over an acid ion exchange resin which is located in the bottom of the column. The dissociation of the ether in this case takes place in the bottom of the column, i.e. the catalyst is continually surrounded by a mixture of ether, olefin and alcohol. This is a disadvantage for the preparation of isobutene, since higher oligomers of isobutene are easily formed at relatively high temperatures under the acidic conditions. In addition, the acid centers of the catalyst are occupied by methanol, which leads to undesirable formation of dimethyl ether. For this reason, a different route is taken in DE 4 322 712. There, the tertiary ether is fed into a reaction distillation column above the reaction zone, and the enrichment section of the column serves for purifying the isobutene while methanol is separated from the MTBE-methanol azeotrope in the stripping section of the column. The azeotrope goes back into the reaction zone. As acid catalyst, use is made of a sulfated titanium dioxide extrudate. DE 100 20 943 discloses an alternative process in which the ether to be dissociated (e.g. MTBE) is introduced into a reactive distillation column below the reaction zone. The actual dissociation takes place in an azeotrope of the ether with the corresponding alcohol.

If the dissocation reactor (7) and the column (9) are configured as a reactive distillation in the process of the invention, preference is given to using structured catalytic multi-purpose packing as described, for example, in U.S. Pat. No. 5,348,710, EP 0 950 433, EP 0 428 265, EP 433 222. Such structured packing which can be used for the purposes of the process of the invention is, for example, commercially available as Katapak® from Sulzer AG, Katamax® from Koch-Glitsch or Multipak® from Montz GmbH. These types of packing are customarily constructed of sheet metal, preferably mild steel, stainless steel, Hastelloy, copper or aluminum, or structured sheets of mesh.

The dissociation mixture comprising unreacted MTBE, methanol, isobutene, low boilers and high boilers is separated in a column ((9) in FIG. 1) into an isobutene-containing top product and a bottom product comprising the unreacted MTBE and the major part of the methanol from the dissociation.

In a further process variant, it is also possible to fractionate the bottom product from the column (9) (FIG. 1) in an additional column (not shown in FIG. 1) to give an MTBE-rich bottom product and a top product comprising mainly an MTBE/methanol azeotrope. Part of this bottom product can be bled off to remove high boilers. The other part is returned to the dissociation stage.

If desired, the bottom product from column (9) or the reactive distillation column can be fed to the synthesis stage of an MTBE plant.

The isobutene which has been separated off from the reaction mixture by distillation comprises methanol, water and dimethyl ether. If desired, methanol is removed therefrom by extraction with water using methods known per se.

The isobutene-containing stream can be fractionated in a purification column to give a bottom product consisting of high-purity isobutene and a top product comprising isobutene, low-volatility by-products and possibly water. This purification column can likewise be preceded by a water scrub to remove methanol.

It is also possible to remove the water present in the isobutene-containing stream which has been separated off (in particular after a scrubbing stage) by means of a decanter. In the decanter, a feed stream comprising isobutene, DME and water is separated into a heavy, aqueous phase and a light, organic phase comprising isobutene and DME.

In the process of the invention, this is preferably carried out using a column provided with a decanter for the removal of water located in the side stream from the colum. Locating the decanter in the side stream minimizes the isobutene losses. It is also possible to install the decanter at the top of the column.

Figure 2:
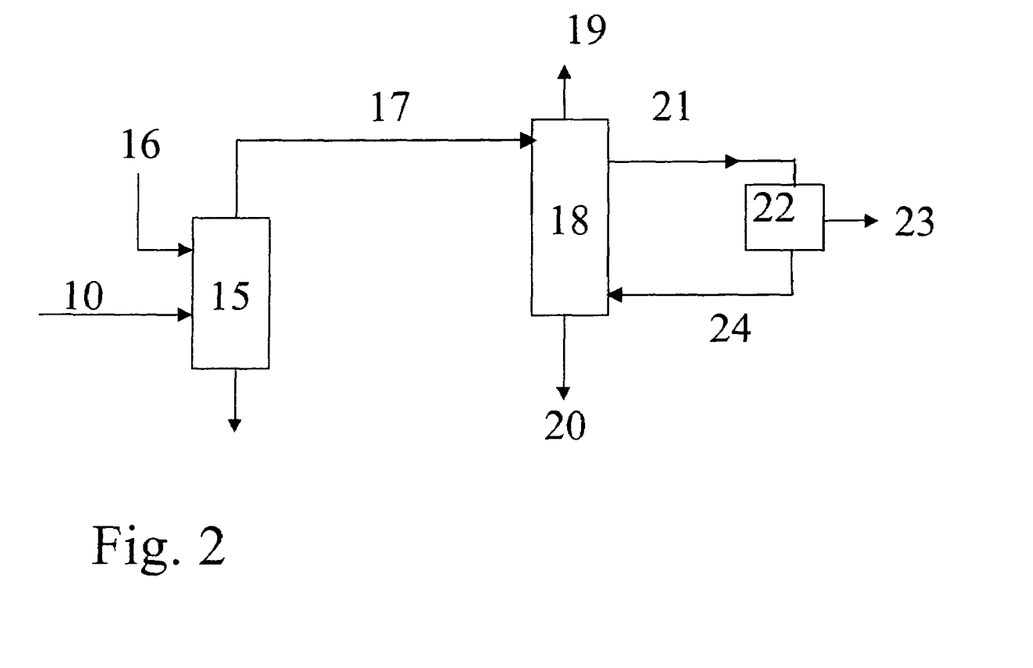
FIG. 2 shows a process carried out with a column provided with a decanter.

FIG. 2 schematically shows such a procedure. The isobutene-containing stream (10) obtained, for example, as shown in FIG. 1 is scrubbed with water (16) in the extractor (15). This isobutene stream (17) which further comprises dimethyl ether and water is fed into the column (18) from which dimethyl ether is taken off as top product (19) and high-purity isobutene is taken off as bottom product (20). A liquid side stream (21) is taken off below the feed point and is separated in the decanter (22) into an aqueous phase (23) and an organic phase (24) which has been depleted in water. Water (23) is taken off and the organic phase (24) is recirculated to the column.

The pure isobutene column (18) preferably has from 25 to 50 theoretical plates, in particular 30-40 theoretical plates. The isobutene to be purified is fed into the 15th to 30th theoretical plate, in particular into the 18th to 24th theoretical plate, in each case counted from the bottom. At a point located from two to five theoretical plates below the feed point, the entire condensate of this theoretical plate is taken off and passed to the decanter. After the water has been separated off by mechanical means, the organic phase is returned to the column at a point which is from one to two theoretical plates further down.

In a particular embodiment of the water removal, the decanter (22) is configured as a decantation tray within the column, e.g. in the top section. In this case, only the aqueous phase is obtained as side stream.

The distillation can be carried out at pressures of from 8 to 20 bar, in particular from 8 to 12 bar. The distillation temperatures are dependent on the pressure. For example, the temperature at the top at 9 bar is about 40° C.

The isobutene obtained by the process of the invention has a purity of from 99.90 to 99.98% by mass. in particular from 99.94 to 99.98% by mass, very particularly preferably from 99.96 to 99.98% by mass.

In the process of the invention, internals comprising trays, random packing or ordered packing can be used for the distillation (column (2), (9) in FIG. 1; column (18) in FIG. 2). In the case of column trays, the following types are used: trays having holes or slits in the baseplate, trays having necks or chimneys covered by bells, caps or hoods, trays having holes in the baseplate which are covered by movable valves. It is also possible to use disordered beds of various packing elements. They can be made of virtually all materials, e.g. steel, stainless steel, copper, carbon, stoneware, porcelain, glass, plastics, etc., and can have various shapes, e.g. spheres, rings having smooth or profiled surfaces, rings having internal webs or openings through the wall, wire mesh rings, saddles and spirals. Packing having a regular geometry can be made of, for example, metal sheets or meslhes. Examples of such packing are Sulzer mesh packing BX made of metal or plastic, Sulzer lamellar packing Mellapack made of sheet metal, structured packing from Sulzer (Optiflow), Montz (BSH) and Kuhni (Rombopack).

The following examples illustrate the invention without restricting its scope which is defined by the description and the claims.

EXAMPLE 1

Dissociation of MTBE with Isobutene and Methanol Being Separated Off

The dissociation of MTBE and the separation of the isobutene produced and the methanol from the unreacted MTBE were carried out in a plant as shown in FIG. 1 but without the MTBE synthesis stage (13). The MTBE-methanol azeotrope and the $C_4$- and $C_5$-hydrocarbon components were separated off using a column (2) which was packed with Sulzer BX mesh packing and had 30 theoretical plates. The enrichment section had an internal diameter of 50 mm and 15 theoretical plates and the stripping section had an internal diameter of 80 mm and likewise 15 theoretical plates. The isobutene was separated off in a column (9) having an internal diameter of 50 mm which was likewise equipped with Sulzer BX mesh packing and had 35 theoretical plates. The dissociation of MTBE was carried out using a tube reactor (7) having an internal diameter of 21 mm and a length of 160 mm. As catalyst, use was made of a commercial ion exchange resin from Bayer, Lewatit K2621. The tube reactor was operated in a thermostated oil bath at 100° C.

The operating parameters of the two columns and the reactor were as follows:

|  |  | Azeotrope column (2) | Isobutene column (9) |  |  | Dissociation reactor (7) |
|---|---|---|---|---|---|---|
| Pressure | bar | 10 | 5 | Pressure | bar | 20 |
| Temperature |  |  |  | Temperature | ° C. | 100 |
| Top | ° C. | 128 | 42 | MTBE conversion | % | 16 |
| Feed | ° C. | 135 | 84 |  |  |  |
| Bottom | ° C. | 148 | 106 |  |  |  |
| Feed plate from the bottom |  | 15 | 20 |  |  |  |
| Reflux ratio | kg/kg | 4 | 3 |  |  |  |

The amounts and compositions of the individual streams are shown in the following tables. industrial MTBE (Driveron®) was used as feed.

|  |  | MTBE feed (1) | Column (2) distillate (3) | Column (2) bottoms (4) | Reactor feed (5) | Bleed stream (6) | Reactor product (8) | Column (9) distillate (10) | Column (9) bottoms (11) |
|---|---|---|---|---|---|---|---|---|---|
| Mass flow | kg/h | 8.0 | 3.6 | 22.5 | 20.2 | 2.2 | 20.2 | 2.1 | 18.1 |
| Proportion by mass |  |  |  |  |  |  |  |  |  |
| Dimethyl ether | kg/kg | 0.00000 | 0.00000 | 0.00000 | 0.00000 | 0.00000 | 0.00005 | 0.00048 | 0.00000 |
| Isobutane | kg/kg | 0.00025 | 0.00055 | 0.00000 | 0.00000 | 0.00000 | 0.00000 | 0.00000 | 0.00000 |
| Isobutene | kg/kg | 0.00000 | 0.00005 | 0.00000 | 0.00000 | 0.00000 | 0.10185 | 0.96873 | 0.00001 |

-continued

|  |  | MTBE feed (1) | Column (2) distillate (3) | Column (2) bottoms (4) | Reactor feed (5) | Bleed stream (6) | Reactor product (8) | Column (9) distillate (10) | Column (9) bottoms (11) |
| --- | --- | --- | --- | --- | --- | --- | --- | --- | --- |
| 1-Butene | kg/kg | 0.00010 | 0.00022 | 0.00000 | 0.00000 | 0.00000 | 0.00000 | 0.00000 | 0.00000 |
| n-Butane | kg/kg | 0.00010 | 0.00022 | 0.00000 | 0.00000 | 0.00000 | 0.00000 | 0.00000 | 0.00000 |
| trans-2-butene | kg/kg | 0.00025 | 0.00055 | 0.00000 | 0.00000 | 0.00000 | 0.00000 | 0.00000 | 0.00000 |
| cis-2-butene | kg/kg | 0.00030 | 0.00066 | 0.00000 | 0.00000 | 0.00000 | 0.00000 | 0.00000 | 0.00000 |
| C5-hydrocarbons | kg/kg | 0.00200 | 0.00437 | 0.00007 | 0.00007 | 0.00007 | 0.00007 | 0.00000 | 0.00008 |
| MTBE | kg/kg | 0.97840 | 0.67047 | 0.97346 | 0.97346 | 0.97346 | 0.81498 | 0.00000 | 0.91072 |
| 2-Methoxybutane | kg/kg | 0.00300 | 0.00284 | 0.00610 | 0.00610 | 0.00610 | 0.00610 | 0.00000 | 0.00682 |
| Methanol | kg/kg | 0.00600 | 0.31706 | 0.00005 | 0.00005 | 0.00005 | 0.05759 | 0.03036 | 0.06079 |
| tert-butanol | kg/kg | 0.00800 | 0.00000 | 0.00945 | 0.00945 | 0.00945 | 0.00733 | 0.00000 | 0.00820 |
| Water | kg/kg | 0.00010 | 0.00295 | 0.00000 | 0.00000 | 0.00000 | 0.00053 | 0.00043 | 0.00054 |
| Diisobutene | kg/kg | 0.00150 | 0.00005 | 0.01087 | 0.01087 | 0.01087 | 0.01150 | 0.00000 | 0.01285 |

EXAMPLE 2

Figure 3:
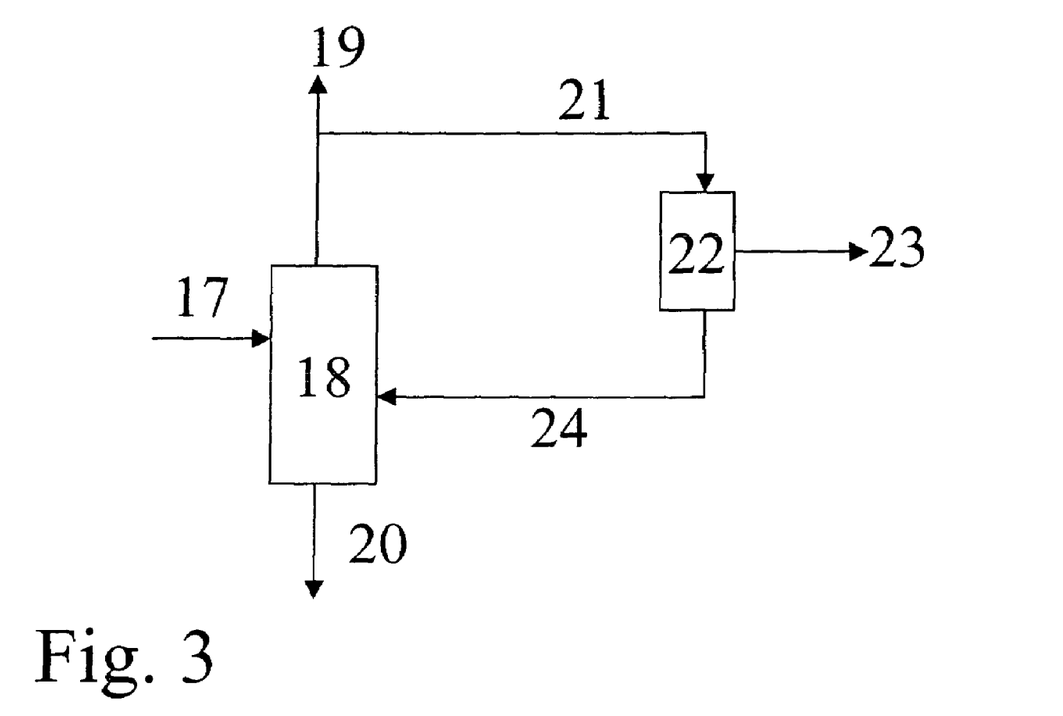
FIG. 3 shows a block diagram for the purification for isobutene removal by dimethyl ether and water.

Removal of DME and Water from the Isobutene Using a Decanter at the Top of the Column The purification of the isobutene by removal of dimethyl ether and water was carried out as shown in FIG. 3 in a column having a diameter of 50 mm. The column was equipped with Sulzer BX mesh packing and had 35 theoretical plates. The decanter (22) from which an aqueous phase (23) was taken off was located at the top of the column (18). The feed to the plant came from an MTBE dissociation (e.g. as shown in FIG. 1) with downstream removal of methanol by extraction with water.

Operating parameters of the column:

|  |  | DME column (18) |
| --- | --- | --- |
| Pressure | bar | 9 |
| Temperature |  |  |
| Top | ° C. | 57 |
| Feed | ° C. | 60 |
| Bottoms | ° C. | 67 |
| Feed plate from the bottom |  | 20 |
| Reflux ratio | kg/kg | 43 |

Flow data:

This experiment, in which the operation parameters had been optimized in terms of isobutene purity and yield, showed that the maximum dimethyl ether concentration in the distillate is limited to about 30% by weight. As a result, about 2.5% of the isobutene is lost via the distillate stream. This amount of loss cannot be reduced using this decanter arrangement.

EXAMPLE 3

Removal of DME and Water from the Isobutene Using a Decanter Located at the Side These experiments were carried out as shown in FIG. 2 using the same column as in Example 2, but the decanter was located below the feed plate.

Operating parameters of the column:

|  |  | DME column (18) |
| --- | --- | --- |
| Pressure | bar | 9 |
| Temperature |  |  |
| Top | ° C. | 41 |
| Feed | ° C. | 60 |
| Bottom | ° C. | 67 |
| Feed (17) to |  | 21 |
| side stream (21) from |  | 15 |

|  |  | Feed column (17) | Distillate from column (19) | Bottoms from column (20) | Feed to decanter (21) | Stream taken off from decanter (23) | Rumback from decanter (24) |
| --- | --- | --- | --- | --- | --- | --- | --- |
| Mass flow | Kg/h | 6.000 | 0.199 | 5.798 | 8.736 | 0.002 | 8.733 |
| Proportion by mass |  |  |  |  |  |  |  |
| Dimethyl ether | kg/kg | 0.01000 | 0.29995 | 0.00003 | 0.20378 | 0.04311 | 0.20382 |
| Isobutene | kg/kg | 0.98930 | 0.69278 | 0.99987 | 0.78859 | 0.00226 | 0.78879 |
| C5-hydrocarbons | kg/kg | 0.00010 | 0.00000 | 0.00010 | 0.00000 | 0.00000 | 0.00000 |
| Methanol | kg/kg | 0.00001 | 0.00013 | 0.00000 | 0.00017 | 0.00190 | 0.00017 |
| Water | kg/kg | 0.00060 | 0.00714 | 0.00000 | 0.00746 | 0.95273 | 0.00721 |

-continued

|  |  | DME column (18) |
|---|---|---|
| recycle (24) to *from the bottom |  | 14 |
| Reflux ratio | kg/kg | 170 |

Stream data:

|  |  | Feed column (17) | Distillate from column (19) | Bottoms from column (20) | Feed to decanter (21) | Stream taken off from decanter (23) | Rumback from decanter (24) |
|---|---|---|---|---|---|---|---|
| Mass flow | Kg/h | 6.000 | 0.063 | 5.933 | 19.003 | 0.004 | 19.000 |
| Proportion by mass |  |  |  |  |  |  |  |
| Dimethyl ether | Kg/kg | 0.01000 | 0.94949 | 0.00003 | 0.00556 | 0.00117 | 0.00556 |
| Isobutene | Kg/kg | 0.98930 | 0.05051 | 0.99987 | 0.99329 | 0.00179 | 0.99348 |
| C5-hydrocarbons | Kg/kg | 0.00010 | 0.00000 | 0.00010 | 0.00005 | 0.00000 | 0.00005 |
| Methanol | Kg/kg | 0.00001 | 0.00000 | 0.00000 | 0.00031 | 0.00823 | 0.00031 |
| Water | Kg/kg | 0.00060 | 0.00000 | 0.00000 | 0.00079 | 0.98881 | 0.00060 |

It can be seen from Example 3 that dimethyl ether concentrations of greater than 95% by weight can be achieved in the distillate by means of the particular arrangement of the decanter and virtually no isobutene losses therefore occur. Thus, better economics than in Example 2 are obtained.

The invention claimed is:

1. A process for preparing isobutene by acid-catalyzed dissociation of methyl tert-butyl ether (MTBE), said process comprising:
    fractionating a feed mixture comprising MTBE, $C_4$- and $C_5$-hydrocarbons, methanol, methyl sec-butyl ether, TBA and $C_4$ oligomers to form a product consisting of
    a) a fraction a), comprising MTBE, MSBE, TBA and C4 oligomers. and
    b) a fraction b), comprising C4- and C5-hydrocarbons, MTBE and methanol, dissociating by an acid-catalyzed reaction the MTBE present in the fraction a) to form a dissociation product comprising methanol and isobutene, and separating the dissociation product to form a separation product c) which comprises unreacted MTBE, methanol, isobutene and low boilers and high boilers in a column into an isobutene-containing top product and a bottom product comprising the unreacted MTBE and the major part of the methanol from the dissociation, and recirculating the bottom product to the feed mixture.

2. The process as claimed in claim 1, wherein the $C_4$ oligomers, MSBE and TBA are separated off from the fraction a) by means of a distillation, in which they are taken off as bottom product.

3. The process as claimed in claim 1, wherein the $C_4$ oligomers, MSBE and TBA are separated off from the fraction a) by means of a bleed stream.

4. The process as claimed in claim 1, wherein the isobutene-containing stream, which has been separated off from the dissociation product is fractionated in a purification column to give a bottom product consisting of pure isobutene and a top product comprising isobutene and volatile by-products.

5. The process as claimed in claim 1, wherein the isobutene-containing stream, which has been separated off from the dissociation product is scrubbed with water, and subsequently fractionated in a purification column to give a bottom product consisting of pure isobutene and a top product comprising isobutene and volatile by-products.

6. The process as claimed in claim 4, wherein water present in the isobutene-containing stream is removed by means of a decanter.

7. The process as claimed in claim 4, wherein water present in the isobutene-containing stream is removed by means of a decanter located in the top section of the purification column.

8. The process as claimed in claim 4, wherein water present in the isobutene-containing stream is removed by means of a decanter which is located at a the side offtake of the purification column.

9. The process as claimed in claim 1, wherein the dissociation and the separation of the isobutene from the MTBE present in the fraction a) are carried out in a reactive distillation column.

10. The process as claimed in claim 2, wherein the isobutene-containing stream, which has been separated off from the dissociation product is fractionated in a purification column to give a bottom product consisting of pure isobutene and a top product comprising isobutene and volatile by-products.

11. The process as claimed in claim 3, wherein the isobutene-containing stream, which has been separated off from the dissociation product is fractionated in a purification column to give a bottom product consisting of pure isobutene and a top product comprising isobutene and volatile by-products.

12. The process as claimed in claim 2, wherein the isobutene-containing stream, which has been separated off from the dissociation product is scrubbed with water, and subsequently fractionated in a purification column to give a bottom product consisting of pure isobutene and a top product comprising isobutene and volatile by-products.

13. The process as claimed in claim 3, wherein the isobutene-containing stream, which has been separated off from the dissociation product is scrubbed with water, and subsequently fractionated in a purification column to give a bottom product consisting of pure isobutene and a top product comprising isobutene and volatile by-products.

14. The process as claimed in claim 5, wherein water present in the isobutene-containing stream is removed by means of a decanter.

15. The process as claimed in claim 5, wherein water present in the isobutene-containing stream is removed by means of a decanter located in the top section of the purification column.

16. The process as claimed in claim 6, wherein the water present in the isobutene-containing stream is removed by means of a decanter located in the top section of the purification column.

17. The process as claimed in claim 5, wherein water present in the isobutene-containing stream is removed by means of a decanter which is located at a side offtake of the purification column.

18. The process as claimed in claim 6, wherein the water present in the isobutene-containing stream is removed by means of a decanter which is located at a side offtake of the purification column.

19. The process as claimed in claim 7, wherein the water present in the isobutene-containing stream is removed by means of a decanter which is located at a side offtake of the purification column.

20. The process as claimed in claim 2, wherein the dissociation and the separation of the isobutene from the MTBE present in fraction a) are carried out in a reactive distillation column.

* * * * *